United States Patent [19]

Steinmann

[11] Patent Number: 5,324,804
[45] Date of Patent: Jun. 28, 1994

[54] PHOTORESIST MATERIAL BASED ON POLYSTYRENES

[75] Inventor: Alfred Steinmann, Praroman, Switzerland

[73] Assignee: Ciba-Geigy Corporation, Ardsley, N.Y.

[21] Appl. No.: 51,720

[22] Filed: Apr. 22, 1993

[30] Foreign Application Priority Data

Apr. 29, 1992 [CH] Switzerland ............... 1378/92

[51] Int. Cl.$^5$ ............................................. C08F 12/24
[52] U.S. Cl. .................................. 526/313; 526/270; 526/271; 526/262; 526/265
[58] Field of Search ............... 526/313, 270, 271, 262, 526/265, 313, 314, 265

[56] References Cited

U.S. PATENT DOCUMENTS

| | | | |
|---|---|---|---|
| 4,491,628 | 1/1985 | Ito et al. .................... | 430/176 |
| 5,069,997 | 2/1991 | Schwalm et al. ............ | 430/270 |
| 5,262,502 | 11/1993 | Fujisawa et al. ........... | 526/313 |

FOREIGN PATENT DOCUMENTS

| | | | |
|---|---|---|---|
| 57-44608 | 3/1982 | Japan ......................... | 526/313 |
| 57-44609 | 3/1982 | Japan ......................... | 526/313 |
| 61-163913 | 7/1986 | Japan ......................... | 526/313 |
| 62-179519 | 8/1987 | Japan ......................... | 526/313 |
| 63-312307 | 12/1988 | Japan ......................... | 526/313 |
| 63-312308 | 12/1988 | Japan ......................... | 526/313 |
| 64-6075 | 1/1989 | Japan ......................... | 526/313 |
| 4-53807 | 2/1992 | Japan ......................... | 526/313 |
| 9205209 | 4/1992 | World Int. Prop. O. ......... | 526/313 |

OTHER PUBLICATIONS

J. Appl. Pol. Sci. 42, 877(1991).

*Primary Examiner*—Joseph L. Schofer
*Assistant Examiner*—N. Sarofin
*Attorney, Agent, or Firm*—William A. Teoli, Jr.

[57] ABSTRACT

Compounds of formula (I)

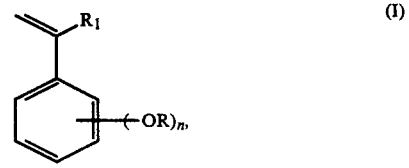

wherein $R_1$ is hydrogen, methyl or halogen, n is 2 or 3, and R is $C_1$–$C_6$alkyl, benzyl, 2-tetrahydrofuranyl, 2-tetrahydropyranyl, $C_1$–$C_6$alkoxycarbonyl, phenoxycarbonyl or benzyloxycarbonyl, or, if two substituents OR are ortho-positioned to each other, two substituents R together form an ethylene group which may be substituted by up to four $C_1$–$C_6$alkyl groups, or form a $C_2$–$C_6$alkylidene group, can be polymerized in the absence or presence of other unsaturated comonomers to polymers having a molecular weight $M_w$ of $10^3$ to $10^6$ and which are suitable for producing positive photoresists with high resolution and very good contrast.

5 Claims, No Drawings

PHOTORESIST MATERIAL BASED ON POLYSTYRENES

The present invention relates to novel styrene derivatives, to homo- and copolymers prepared therefrom, to radiation-sensitive compositions containing said polymers, and to the use of such compositions as photoresists for producing printed circuits.

Positive- and negative-working photoresist compositions based on poly[p-tert-butoxycarbonyloxystyrene] and onium salts, suitable for lithography in the deep UV range (DUV, wavelengths of c. 200–300 nm) are disclosed, inter alia, in U.S. Pat. No. 4,491,628.

Similar resist compositions containing poly[p-2-tetrahydropyranyloxy]styrene are disclosed in EP-A 342 498.

These compositions, however, require rather high exposure energies, which is a disadvantage in the industrial production of printed circuits.

In the publication "Tetrahydropyranyl- and Furanyl-Protected Polyhydroxystyrene in Chemical Amplification Systems" by S. A. M. Hesp, N. Hayashi and T. Ueno in J. Appl. Pol. Sci. 42, 877 (1991), it is disclosed that poly[p-(tetrahydrofuranyloxy)styrene] and poly[p-(tetrahydropyranyloxy)styrene] are suitable for the production of positive photoresists having high sensitivity and resolution in the submicron range. However, the photoresists described in this publication cannot be developed in pure aqueous-alkaline media, but only with the addition of n-propanol.

It has now been found that positive photoresists that are developable in aqueous-alkaline media can be obtained by using as base resins polystyrenes in which the aromatic nuclei are substituted by two or three acid generating groups.

Accordingly, the invention relates to compounds of formula (I)

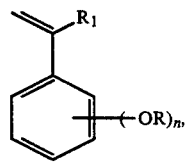

wherein $R_1$ is hydrogen, methyl or halogen, n is 2 or 3, and R is $C_1$–$C_6$alkyl, benzyl, 2-tetrahydrofuranyl, 2-tetrahydropyranyl, $C_1$–$C_6$alkoxycarbonyl, phenoxycarbonyl or benzyloxycarbonyl, or, if two substituents OR are ortho-positioned to each other, two substituents R together form an ethylene group which may be substituted by up to four $C_1$–$C_6$alkyl groups, or form a $C_2$–$C_6$alkylidene group.

$R_1$ as halogen is preferably chloro or bromo.

R defined as $C_1$–$C_6$alkyl or $C_1$–$C_6$alkoxycarbonyl denotes straight-chain or, preferably, branched radicals.

Illustrative examples $C_1$–$C_6$alkyl radicals are methyl, ethyl, n-propyl, isopropyl, n-butyl, n-pentyl, neopentyl, n-hexyl or, preferably, tert-butyl.

$C_1$–$C_6$Alkoxycarbonyl groups are typically methoxycarbonyl, ethoxycarbonyl, n-propoxycarbonyl, isopropoxycarbonyl, n-butoxycarbonyl, n-pentoxycarbonyl, neopentoxycarbonyl, n-hexoxycarbonyl or, preferably, tert-butoxycarbonyl.

Unsubstituted or substituted ethylene groups are typically ethylene, propylene, 1,2-dimethylethylene and tetramethylethylene.

$C_2$–$C_6$Alkylidene groups are typically ethylidene, propylidene and isopropylidene.

Preferred compounds of formula (I) are those wherein $R_1$ is hydrogen, n is 2 and both substituents OR are in 3,4- or 3,5-position to the vinyl group.

Particularly preferred compounds of formula (I) are those wherein $R_1$ is hydrogen, n is 2, both substituents OR are in 3,4- or 3,5-position to the vinyl group, and R is tert-butoxycarbonyl, 2-tetrahydrofuranyl or 2-tetrahydropyranyl.

The compounds of formula (I) can be synthesised by known methods from the di- or trihydroxy compounds of formula (II)

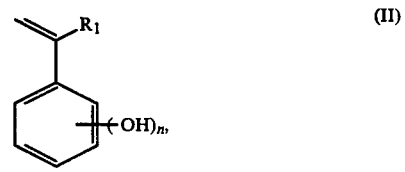

wherein $R_1$ and n are as defined for formula (I).

The compounds of formula (I), wherein R is $C_1$–$C_6$alkyl or benzyl, may be prepared by reacting compounds of formula (II) with the corresponding alkyl or benzyl halides or tosylates or dialkyl or dibenzyl sulfates in alkaline solution.

The compounds of formula (I), wherein R is $C_1$–$C_6$alkoxycarbonyl, phenoxycarbonyl or benzyloxycarbonyl, are obtainable from the compounds of formula (II) by reaction with the corresponding dialkyl, diphenyl and dibenzyl carbonates in the presence of bases.

The compounds of formula (I), wherein R is 2-tetrahydrofuranyl or 2-tetrahydropyranyl, can be prepared from the compounds of formula (II) by reaction with 2,3-dihydrofuran or 2,3-dihydropyran in acid solution.

The compounds of formula (I), wherein two substituents R together form an ethylene group which may be substituted by up to four $C_1$–$C_6$alkyl groups, or form a $C_2$–$C_6$alkylidene group, are obtainable from the compounds of formula (II) carrying two ortho-positioned OH groups by reaction with the corresponding aldehydes or ketones under acid conditions.

The compounds of formula (II) may be prepared in a multi-step synthesis from the di- or trihydroxybenzoic acids of formula (III)

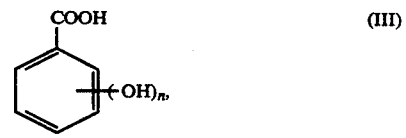

wherein n is 2 or 3.

In this reaction, the di- or trihydroxybenzoic acids of formula (III) are reacted in a first step with acetic anhydride to the corresponding di- or triacetoxybenzoic acids and then converted with thionyl chloride into the acid chlorides of formula (IV)

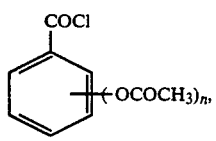

wherein n is 2 or 3.

Reaction of the acid chlorides of formula (IV) with tertiary amines and alkenes of formula (V)

wherein $R_1$ is as defined for formula (I), gives the di- or triacetoxystyrenes of formula (VI)

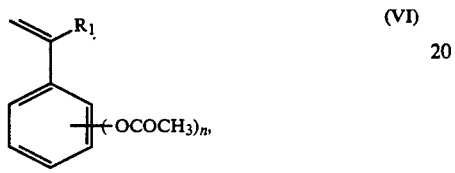

wherein $R_1$ and n are as defined for formula (I), which can then be saponified in known manner to give the di- or trihydroxystyrenes of formula (II).

In some cases the compounds of formula (II) can also be obtained by less elaborate syntheses. Thus, for example, 3,4-dihydroxystyrene can be synthesised by decarboxylation of commercially available caffeic acid (3,4-dihydroxycinnamic acid).

The novel compounds of formula (I) can be polymerised in known manner in the absence or presence of olefinically unsaturated comonomers.

The invention thus also relates to polymers having a molecular weight $M_w$ of $10^3$ to $10^6$ (determined by gel permeation chromatography) and containing, based on the total amount of structural units present in the polymer, 100 to 5 mol % of a structural repeating unit of formula (VII)

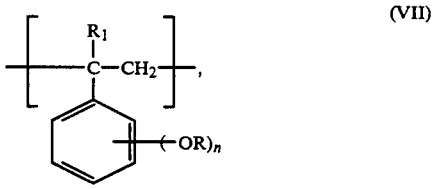

wherein $R_1$, R and n have the given meanings, and 95 to 0 mol % of a structural repeating unit of formula (VIII)

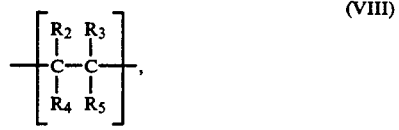

wherein $R_2$ and $R_3$ are each independently of the other hydrogen, $C_1$-$C_4$alkyl which is unsubstituted or substituted by halogen, cyano or nitro, or are phenyl or naphthyl which are unsubstituted or substituted by halogen, $C_1$-$C_4$alkoxy, hydroxy, cyano or nitro, and $R_4$ and $R_5$ are each independently of the other a hydrogen or halogen atom, $C_1$-$C_{12}$alkyl which is unsubstituted or substituted by halogen atoms, cyano or nitro, or are phenyl, naphthyl or benzyl which are unsubstituted or substituted by halogen, cyano or nitro $C_1$-$C_4$alkyl or $C_1$-$C_4$alkoxy, or are a radical selected from the group consisting of $-OR_6$, $-COOR_7$ and $-COR_8$ or, together with a divalent radical of formulae (IX)-(XI) are

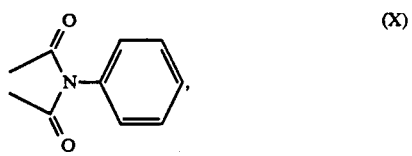

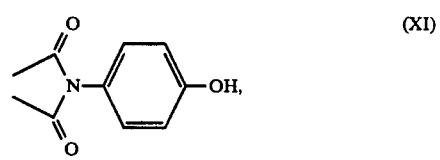

wherein $R_6$ and $R_7$ are each independently of the other hydrogen, $C_1$-$C_{12}$alkyl which is unsubstituted or substituted by halogen, cyano or nitro, or are phenyl or naphthyl, unsubstituted or substituted by halogen, cyano, nitro, $C_1$-$C_4$alkyl or $C_1$-$C_4$alkoxy, and $R_8$ has the same meaning as $R_6$ or is the radical

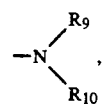

wherein $R_9$ and $R_{10}$ have each independently of the other the same meaning as $R_8$.

$R_2$, $R_3$, $R_4$ and $R_5$ in the structural unit of formula (VIII) defined as alkyl are straight-chain or branched, preferably straight-chain, alkyl radicals.

Halogen substituents are preferably chloro or bromo.

Unsubstituted or substituted alkyl is typically methyl, ethyl, 2-chloroethyl, 2-nitroethyl, n-propyl, isopropyl, n-butyl, sec-butyl, tert-butyl, n-pentyl, isoamyl, n-hexyl, 2-ethylhexyl, n-decyl, 6-nitrohexyl or 9-bromononyl.

Illustrative examples of substituted phenyl or naphthyl are o-, m- or p-chlorophenyl, o-, m- or p-tolyl, xylyl, 2-nitrophenyl or α-chloronaphthyl.

$R_2$, $R_3$ and $R_4$ in the structural unit of formula (VIII) are each independently of one another preferably hydrogen, $C_1$-$C_6$alkyl or phenyl, and $R_5$ is preferably halogen, phenyl or benzyl or a radical selected from the group consisting of $-OR_6$, $-COOR_7$ and $-COR_8$, wherein $R_6$, $R_7$ and $R_8$ are each independently of one another hydrogen, $C_1$-$C_6$alkyl or phenyl, and $R_8$ may also be the radical

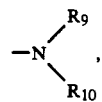

wherein $R_9$ and $R_{10}$ have each independently of the other the preferred meaning of $R_6$.

The novel polymers preferably have a molecular weight $M_w$ of 5 000 to 500 000, most preferably of 20 000 to 150 000.

The novel polymers also preferably contain 100 to 20 mol %, most preferably 100 to 50 mol %, of a structural repeating unit of formula (VII) and 80 to 0 mol %, most preferably 50 to 0 mol %, of a structural repeating unit of formula (VIII).

Particularly preferred polymers contain 100 mol % of a structural repeating unit of formula (VII).

Very particularly preferred polymers of this invention are those containing a structural repeating unit of formula (VII), wherein $R_1$ is hydrogen, n is 2 and both substituents OR are in 3,4- or 3,5-position to the vinyl group.

The substituent R in formula (VII) is preferably tert-butoxycarbonyl, 2-tetrahydrofuranyl or 2-tetrahydropyranyl.

The invention further relates to a process for the preparation of polymers containing, based on the total amount of structural units present in the polymer, 100 to 5 mol %, of a structural repeating unit of formula (VII) and 95 to 0 mol % of a structural repeating unit of formula (VIII), which process comprises subjecting a compound of formula (I) or a mixture of a compound of formula (I) and compounds of formula (XII)

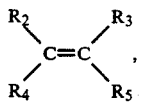
(XII)

present therein in an amount of up to 95 mol %, wherein $R_2$, $R_3$, $R_4$ and $R_5$ have the meanings assigned to them above, to radical polymerisation.

The radical polymerisation can be carried out using different techniques. These techniques are described, inter alia, by S. Sandler and W. Karo in "Polymer Synthesis" Vol. 1-3, 1968, Academic Press, New York. Standard polymerisation methods are typically mass polymerisation or solvent, emulsion, suspension or precipitation polymerisation.

The compounds of formula XII are known and some are commercially available. Besides olefins such as ethylene or propylene, examples of compounds of formula XII are especially the vinyl compounds. Exemplary of such monomers are the styrene types such as styrene, α-methylstyrene, p-methylstyrene, p-hydroxystyrene, p-acetylstyrene or p-hydroxyphenylstyrene, α,β-unsaturated acids and their esters or amides, including acrylic acid, methyl acrylate, acrylamide, the corresponding methacrylic compounds, methyl maleate, maleimide, p-hydroxyphenylmaleimides or tert-butyl 4-vinylbenzoate, halogen-containing vinyl compounds, including vinyl chloride, vinyl fluoride, vinylidene chloride and vinylidene fluoride, vinyl esters such as vinyl acetate, or vinyl ethers such as methyl vinyl ether or butyl vinyl ether.

Further suitable compounds include the allyl compounds, such as allyl chloride, allyl bromide or allyl cyanide.

The polymerisation is normally initiated by one of the customary initiators of radical polymerisation. Such initiators include thermal inititiators such as azo compounds, typically azoisobutyronitrile (AIBN), or peroxides, conveniently benzoyl peroxide, or redox initiator systems, for example a mixture of iron(III)acetylacetonate, benzoin and benzoyl peroxide, or photochemical radical formers such as benzoin or benzil methyl ketal.

The polymerisation is preferably carried out in solution. The reaction temperature is normally in the range from 10° to 200° C., preferably from 40° to 150° C. and, most preferably, from 40° to 100° C.

Any solvents present must be inert under the reaction conditions. Suitable solvents include aromatic hydrocarbons, chlorinated hydrocarbons, ketones and ethers. Typical examples of such solvents are benzene, toluene, xylene, ethyl benzene, isopropyl benzene, ethylene chloride, propylene chloride, methylene chloride, chloroform, methyl ethyl ketone, acetone, cyclohexanone, diethyl ether or tetrahydrofuran.

As mentioned at the outset, the polymers of this invention are very useful base resins for DUV photoresists which have very high sensitivity.

Accordingly, the invention also provides radiation-sensitive compositions comprising a) a polymer containing, based on the total amount of structural units present in the polymer, 100 to 5 mol % of a structural repeating unit of formula VII and 95 to 0 mol % of a structural repeating unit of formula VIII, and b) a substance that generates an acid upon exposure to actinic radiation.

A large number of compounds are known as radiation-sensitive components b) which, upon exposure to light, generate an acid. These compounds include, for example, the diazonium salts used in the diazo process, the o-quinone-diazides used in known positive-working copying compositions, or also halogen compounds which form a hydrohalic acid upon irradiation. Compounds of this type are disclosed, inter alia, in U.S. Pat. Nos. 3,515,552, 3,536,489 or 3,779,778, and in DE-OS 2 718 259, 22 43 621 or 2 610 842.

Particularly suitable radiation-sensitive components b) of the compositions of this invention are photoinitiators selected from the group consisting of iodonium or sulfonium salts. Such compounds are described, for example, in "UV-Curing, Science and Technology" (Editor: S. P. Pappas, Technology Marketing Corp., 642 Westover Road, Stanford, Conn., USA).

Sulfoxonium salts can also be used as radiation-sensitive compounds. Such salts are disclosed, for example, in EP patent 35 969 or in EP-A 44 274 and 54 509. Particular mention is made of aliphatic sulfoxonium salts which absorb in the deep UV range.

It is also possible to use those compounds which generate sulfonic acids when irradiated with actinic light. Such compounds are known per se and are described for example, in GB-A 2 120 263, EP-A 84 515, 37 512 or 58 638 and in U.S. Pat. No. 4,258,121 or U.S. Pat. No. 4,371,605.

If salts are used as the radiation-sensitive, acid-releasing components b), then said salts are preferably soluble in organic solvents. Most preferably, these salts are products with complex acids, for example with hydrofluoroboric acid, hexafluorophosphonic acid, hexafluoroarsenic acid or hexafluoroantimonic acid.

It is preferred to use an iodonium, sulfonium or sulfoxonium salt as component (b).

Most preferably, component (b) is selected from the group consisting of triphenylsulfonium hexafluoroarsenate, triphenylsulfonium hexafluoroantimonate and triphenylsulfonium trifluoromethylsulfonate (triphenylsulfonium triflate).

The novel compositions preferably contain, based on the total amount of components (a) and (b), 85-99% by weight, most preferably 92-98% by weight, of component (a) and 1-15% by weight, most preferably 2-8% by weight, of component (b).

If desired, a binder (c) may also be added to the novel radiation-sensitive compositions. This addition is especially useful if the light-sensitive compositions are liquid or low viscosity formulations.

The amount of binder (c) may be 30-90% by weight, preferably 60-90% by weight, based on the total amount of components (a), (b) and (c).

The choice of binder is made according to the field of use and the properties required therefor, such as developability in aqueous and aqueous alkaline solvent systems or adhesion to substrates.

Suitable binders c) are typically novolaks which are derived from an aldehyde, preferably formaldehyde, acetaldehyde or furfuraldehyde, but preferably from formaldehyde, and a phenol. The phenolic component of these binders is preferably phenol itself or also halogenated phenol, for example substituted by one or two chlorine atoms, preferably p-chlorophenol, or it is a phenol substituted by one to two $C_1$-$C_9$alkyl groups, for example o- m- or p-cresol, a xylenol, p-tert-butylphenol or p-nonylphenol. The phenol component of the preferred novolaks may however also be p-phenylphenol, resorcinol, bis(4-hydroxyphenyl)methane or 2,2-bis(4-hydroxyphenyl)propane.

Some of the phenolic hydroxyl groups of these novolaks may be modified by reaction with chloroacetic acid, isocyanates, epoxides or carboxylic anhydrides.

Further suitable binders are poly(4-hydroxystyrene) or copolymers of maleic anhydride with styrene or vinyl ethers or 1-alkenes. Suitable binders are also: homo- and copolymeric acrylates and methacrylates, for example copolymers of methylmethacrylate/ethyl acrylate/methacrylic acid, poly(alkylmethacrylates) or poly(alkylacrylates) in which alkyl is $C_1$-$C_{20}$.

It is preferred to use as binder an alkali-soluble substance, conveniently a novolak (unmodified or modified as described above), poly(4-hydroxystyrene), copolymers of maleic anhydride with styrene or vinyl ethers or 1-alkenes, as well as copolymers of esters of acrylic acid or of methacrylic acid with ethylenically unsaturated acids, such as methacrylic acid or acrylic acid.

The alkali-soluble binders may contain further additional resins as is customary for positive systems based on diazo ketone. These additional resins include typically vinyl polymers such as polyvinyl acetate, polyacrylates, polyvinyl ethers or polyvinyl pyrrolidones. Usually, however, not more than 20% by weight, based on the amount of alkali-soluble binder, of these additional resins is added.

The compositions of this invention may contain further conventional modifiers such as stabilisers, pigments, dyes, fillers, adhesion promoters, flow control agents, wetting agents and plasticisers. For application, the compositions may also be dissolved in suitable solvents.

The compositions of this invention have excellent suitability as coating agents for substrates of all kinds, for example wood, textiles, paper, ceramics, glass, plastics materials such as polyesters, polyethylene terephthalate, polyolefins or cellulose acetate, preferably in the form of films, and also of metals such as Al, Cu, Ni, Fe, Zn, Mg or Co, and of GaAs, Si or $SiO_2$, on which it is desired to produce an image by image-wise exposure.

The substrates may conveniently be produced by preparing a solution or suspension of the novel composition.

The choice of solvent and the concentration will depend mainly on the nature of the composition and on the coating method. The solution is uniformly applied to a substrate by known coating methods, for example by spin coating, dip coating, doctor coating, curtain coating, brushing, spraying and reverse roller coating. It is also possible to apply the light-sensitive layer to a temporary flexible support and then to coat the final substrate, for example a copper-clad circuit board, by coat transfer by means of lamination.

The add-on (layer thickness) and the nature of the substrate are contingent on the desired utility. A particular advantage of the compositions of the invention is that they can be used in widely varying layer thicknesses. This thickness range comprises values of c. 0.5 $\mu$m to more than 100 $\mu$m. With conventional positive-working systems based on naphthoquinone diazide, layer thicknesses preferably smaller than 10 $\mu$m can be used.

Possible utilities of the compositions of this invention are as photoresists in the electronics field (galvanoresist, discharge resist, solder resist), the production of printing plates such as offset plates or screen printing formes, mould etching, or as microresist in the production of integrated circuits.

The novel photoresist compositions are distinguished by very high resolution (submicron range). As the base resins (a) contain two or three acid generating groups per styrene unit, the difference in solubility between irradiated and non-irradiated areas and hence the desired contrast is greater than that of comparable known photoresist systems. For this reason, the novel photoresist compositions are especially suitable for making microchips. The invention thus further relates to the use of the novel photoresist compositions as photoresists for making integrated circuits.

In accordance with the numerous utilities, the possible substrates and the processing conditions may differ widely.

Sheets made from polyester, cellulose acetate or plastics-coated papers are typically used for the photographic recording of information. Specially treated aluminium is used for offset formes, and copper-clad laminates are used for producing printed circuits, and siklicon wafers are used for making integrated circuits. The layer thicknesses for photographic materials and offset printing formes are from c. 0.5 $\mu$m to 10 $\mu$m, and for printed circuits 1 to c. 100 $\mu$m.

After the substrate has been coated, the solvent is normally removed by drying to give a layer of photoresist on the substrate.

After image-wise exposure of the material in conventional manner, the exposed areas of the photoresist are washed out with a developer.

The choice of developer depends on the type of photoresist or the photolysis products. The developer may comprise aqueous solutions of bases to which organic solvents or mixtures thereof may be added.

Particularly preferred developers are the aqueous-alkaline solutions used for the development of naphthoquinone diazide layers. These solutions include in particular aqueous solutions of alkali metal silicates, phosphates and hydroxides, carbonates and hydrogen carbonates. These solutions may additionally contain minor amounts of wetting agents and/or organic solvents.

Typical organic solvents which may be added to the developer liquids are cyclohexanone, 2-ethoxyethanol, toluene, acetone, as well as mixtures of two or more of these solvents.

The expression "imagewise" exposure will be understood as meaning exposure through a photomask which contains a predetermined pattern, for example a photographic transparency, exposure by a laser beam which is moved by computer control over the surface of the coated substrate to produce an image, as well as exposure with computer-controlled electron beams or treatment with X-rays through an absorber mask.

Suitable sources of radiation are basically all lamps which emit radiation in the DUV range (c. 200–300 nm). Point light sources as well as arrays of reflector lamps are suitable. Examples are: carbon arcs, xenon arcs, mercury vapour lamps which may be doped with halogen atoms (metal halide lamps), fluorescent lamps, argon glow lamps, electronic flash lamps, photographic flood lamps, electron beams and X-rays. The distance between lamp and image material may vary, depending on the utility and the type and strength of the lamp, for example from 2 cm to 150 cm. Particularly suitable light sources are laser light sources, for example argon ion lasers or crypton ion lasers. With laser light the resist can also be irradiated without a mask, as the controlled laser beam writes direct on to the layer. The high sensitivity of the compositions of the invention is very advantageous here and permits high writing speeds at relatively low intensities. This method can be used to make printed circuits for the electronics industry, lithographic offset plates or relief printing plates as well as photographic image recording materials. The high sensitivity of the resists is also advantageous for irradiating with DUV steppers, as very brief exposure times are desired.

EXAMPLES

I. Preparation of the Monomers

I.1. 3,4-bis(2-tetrahydropyranyloxy)styrene a) Preparation of 3,4-dihydroxystyrene 200 g (1.11 mol) of caffeic acid are dissolved in 1.2 l of dimethyl formamide dissolved and the solution is stirred for 3 h at 150° C. After cooling to room temperature, the solution is poured on to 3 kg of ice, saturated with sodium chloride and extracted twice with ethyl acetate. The organic phase is washed with 2% NaHCO$_3$ solution and then with water, dried over Na$_2$SO$_4$ and concentrated by evaporation, giving 120 g (80%) of a highly viscous liquid which can be recrystallised from toluene. The substance is, however, sufficiently pure and can be further processed without recrystallisation.

Elemental analysis: calcd=C: 70.52, H: 5.97; found=C: 70.25, H: 6.02.

$^1$H-NMR (CDCl$_3$/DMSO): δ=4.99; 5.03; 5.44; 5.51 ppm (dd, 2H); δ=6.47; 6.50; 6.53; 6.56 ppm (m, 1H); δ=6.66–6.74; 6.74; 6.89 (m, 3H); δ=8.53 ppm (s, 1H); δ=8.63 ppm (s, 1H).

b) Preparation of 3,4-bis(2-tetrahydropyranyloxy)styrene

To 100 g (0.73 mol) of the 3,4-dihydroxystyrene prepared in a) are added 320 g (3.8 mol) of dihydropyran and a few drops of concentrated hydrochloric acid. The reaction mixture is stirred for 12 h at 40° C. The solution is then diluted with diethyl ether and poured on to ice. The organic phase is washed twice at 0° C. with 1N NaOH, dried, and treated with activated carbon. After filtration and concentration of the filtrate there is obtained a colourless viscous liquid which is chromatographed over a column of silica gel with a 4:1 mixture of hexane/ethyl acetate.

Yield: 111 g (50%).

Elemental analysis: calcd=C: 71.03, H: 7.95; found=C: 70.86, H: 8.18.

$^1$H-NMR (CDCl$_3$): δ=1.62–2.05 ppm (m, 12H); δ=3.57–3.63 ppm and 3.86–4.12 ppm (m, 4H); δ=5.11–5.14 ppm and 5.57–5.63 ppm (m, 2H); δ=5.41–5.46 ppm (m, 2H); δ=6.57–6.66 ppm (m, 1H); δ=6.97–7.24 ppm (m, 3H).

I.2. 3,4-Bis(2-tetrahydrofuranyloxy)styrene

To 38.1 g (0.28 mol) of 3,4-dihydroxystyrene and 118 g (1.68 mol) of 2,3-dihydrofuran are added 5 drops of concentrated hydrochloric acid, whereupon an exothermic reaction ensues. The solution is stirred for 4 h at 50° C. and then poured on to a mixture of ice-water and diethyl ether. After two extractions with diethyl ether, the organic phase is washed three times at 0° C. with 1N NaOH and dried over Na$_2$SO$_4$. The solvent is removed by evaporation to leave a clear liquid which is purified by distillation in a bulb tube (155° C./0.02 torr) or by column chromatography (silica gel, hexane/ethyl acetate 4:1).

Yield: 47 g (61%).

Elemental analysis: calcd=C: 69.54, H: 7.30; found=C: 69.36, H: 7.44.

$^1$H-NMR (CDCl$_3$): δ=1.84–2.23 ppm (m, 8H); δ=3.89–4.12 ppm (m, 4H); δ=5.10; 5.15 ppm and 5.58; 5.64 ppm (m, 2H); δ=5.75 ppm (m, 2H); δ=6.57–6.66 ppm (m, 1H); δ=6.97–7.24 ppm (m, 3H).

I.3. 3,4-Bis(tert-butoxycarbonyloxy)styrene 38 g (0.28 mol) 3,4-dihydroxstyrene are dissolved in 1 l of tetrahydrofuran and the solution is cooled to 5° C. With stirring and cooling, 63 g (0.56 mol) of potassium tert-butylate are added over 20 min in increments such that the temperature of the mixture remains between 5° C. The mixture is stirred for 1 h at room temperature. Then a solution of 135.3 g (0.62 mol) of di-tert-butylcarbonate in a small amount of THF is added dropwise. After stirring for c. 3 h at room temperature, analysis by thin-layer chromatography (hexane/ethyl acetate 4:1) indicates the end of the reaction. The reaction mixture is poured on to 2 kg of ice and extracted twice with diethyl ether. The organic phase is washed twice with 1N NaOH and then with water, and dried. The solvent is then removed by distillation on a rotary evaporator. The viscous residue is purified by column chromatography (silica gel, hexane/ethyl acetate 4:1).

Yield: 23 g (24%).

Elemental analysis: calcd=C: 64.27, H: 7.19; found=C: 63.90, H: 7.03.

$^1$H-NMR (CDCl$_3$): δ=1.52–1.56 ppm (m, 18H); δ=5.24; 5.28 ppm and 5.66; 5.72 ppm (m, 2H); δ=6.60–6.70 ppm (m, 1H); δ=7.19–7.30 ppm (m, 3H).

I.4. 3,5-Bis(2-tetrahydropyranyloxy)styrene a) Preparation of 3,5-diacetoxybenzoic acid:

50 g (0.32 mol) of 3,5-dihydroxybenzoic acid are added to 100 ml of acetic anhydride. With cooling, a solution of 10 drops of concentrated sulfuric acid in 60 ml of acetic anhydride are slowly added dropwise such that the temperature of the reaction mixture is kept between 20° C. and 25° C. The reaction mixture is stirred for 1 h at room temperature and then poured on to ice-water, whereupon the product precipitates. The crude product is dried and recrystallised from toluene.

Yield: 52 g (57%).
Melting point: 160.4° C.
Elemental analysis: calcd=C: 55.47, H: 4.23; found=C: 55.56, H: 4.24.
$^1$H-NMR (CD$_3$OD): $\delta$=2.28 ppm (s, 6H); $\delta$=4.91 ppm (s, 1H), $\delta$=7.18-7.20 ppm and 7.62-7.64 ppm (m, 3H).

b) Preparation of 3,5-diacetoxybenzoyl chloride:

8.33 g (3.5 mol) of the 3,5-diacetoxybenzoic acid prepared in a), 1 kg (8.4 mol) of thionyl chloride and 3 ml of dimethyl formamide are dissolved in 5.3 l of ethyl acetate and the solution is heated to 70° C. The solution is stirred at this temperature until no more evolution of HCl and SO$_2$ is observed. After evaporation of the solvent, the crude product is recrystallised from cyclohexane.

Yield: 785 g (87%).
Melting point: 90° C.
Elemental analysis: calcd=C: 51.48, H: 3.53, Cl: 13.81; found=C: 51.45, H: 3.68, Cl: 13.70.
$^1$H-NMR (CDCl$_3$): $\delta$=2.31 ppm (s, 6H); $\delta$=7.27-7.29 ppm and 7.72-7.77 ppm (m, 3H).

c) Preparation of 3,5-diacetoxystyrene:

170 g (0.66 mol) of the 3,5-diacetoxybenzoyl chloride prepared in b), 89.6 g (0.66 mol) of N-benzyldimethylaniline, and 1.5 g (6.6 mmol) of palladium(II) acetate are dissolved in 1.7 l of toluene. This solution is reacted in a 3 l autoclave for 10 h at 95° C. wirth ethylene under a pressure of 10 atmospheres. Afterwards, the reaction solution is washed with 1N HCl, with 1N NaOH and then with water. After drying over Na$_2$SO$_4$, the organic phase is decolourised with activated carbon and filtered. The filtrate is concentrated by evaporation, giving 120 g (0.54 mol=82%) of a viscous liquid which can be further processed without purification.

For analysis, the substance can be purified by column chromatography (silica gel, hexane/ethyl acetate 2:1) or by bulb tube distillation (140° C./0.02 torr).

Elemental analysis: calcd=C: 65.45, H: 5.49; found=C: 65.42, H: 5.56.
$^1$H-NMR (CDCl$_3$): $\delta$=2.24 ppm (s, 6H); $\delta$=5.28; 5.32 ppm and 5.69; 5.75 ppm (m, 2H); $\delta$=6.58-6.68 ppm (m, 1H); $\delta$=6.81-7.00 ppm (m, 3H).

d) Preparation of 3,5-dihydroxystyrene:

With stirring and cooling with ice, 20 g (91 mmol) of 3,5-diacetoxystyrene are added to 20 g (357 mmol) of potassium hydroxide in 200 ml of methanol so slowly that a reaction temperature of 30° C. is not exceeded. After a few minutes, a thin-layer chromatogram shows that no more educt is present. The reaction mixture is poured into ice-water and washed with ether. The aqueous phase is acidified at 0° C. with sulfuric acid to pH 1. After two extractions with ether, the organic phase is dried and the solvent is removed by evaporation, giving 10 g (80%) of a solid which can be recrystallised from toluene.

Melting point: 84° C.
Elemental analysis: calcd=C: 70.58, H: 5.92; found=C: 70.26, H: 5.93.

$^1$H-NMR (acetone-d$_6$): $\delta$=5.13; 5.17 ppm and 5.63; 5.69 ppm (m, 2H); $\delta$=6.30; 6.44 ppm (m, 3H); $\delta$=6.54-6.63 ppm (m, 1H); $\delta$=8.2 ppm (s, 2H).

e) Preparation of 3,5-bis(2-tetrahydropyranyloxy)styrene:

0.5 ml of concentrated hydrochloric acid is added to 80 g (587 mmol) of 3,5-dihydroxystyrene in 300 g of dihydropyran and the reaction mixture is stirred for 2 h at 40° C. The mixture is then poured into ice-water and extracted twice with ether. The organic phase is washed three times at 0° C. with 1N NaOH, dried, and concentrated by evaporation. The residue is purified by column chromatography (silica gel, hexane/ethyl acetate 4:1), giving 110 g (62%) of a viscous liquid.

Elemental analysis: calcd=C: 71.03, H: 7.95; found=C: 70.96, H: 8.03.
$^1$H-NMR (CDCl$_3$): $\delta$=1.54-2.04 ppm (m, 12H); $\delta$=3.52-3.95 ppm (m, 4H); $\delta$=5.19; 5.23 ppm and 5.67; 5.73 ppm (m, 2H); $\delta$=5.39-5.43 ppm (m, 2H); $\delta$=6.57-6.67 ppm (m, 1H); $\delta$=6.70-6.76 ppm (m, 3H).

I.5. 3,5-Bis(2-tetrahydrofuranyloxy)styrene

To a mixture of 45 g (330 mmol) of 3,4-dihydroxystyrene and 140 g of 2,3-dihydrofuran are added 5 drops of concentrated hydrochloric acid, whereupon an exothermic reaction ensures. The mixture is stirred for about 3 h at 40°-45° C. and then poured on to ice-water. After two extractions with ether, the organic phase is washed three times with 1N NaOH, dried, treated with activated carbon and filtered. The solvent is removed by evaporation to leave a clear liquid which is purified by column chromatography (silica gel, hexane/ethyl acetate 4:1).

Yield: 40 g (44%).
Elemental analysis: calcd=C: 69.55, H: 7.30; found=C: 69.07, H: 7.59.
$^1$H-NMR (CDCl$_3$): $\delta$=1.84-2.17 ppm (m, 8H); $\delta$=3.82-4.07 ppm (m, 4H); $\delta$=5.19; 5.23 ppm and 5.67; 5.73 ppm (m, 2H); $\delta$=5.77-5.80 ppm (m, 2H); $\delta$=6.56-6.64 ppm (m, 1H); $\delta$=6.64-6.73 ppm (m, 3H).

I.6. 3,5-Bis(tert-butyloxycarbonyloxy)styrene

A solution of 43 g (320 mmol) of 3,5-dihydroxystyrene in 1 l of THF is placed in a reactor under nitrogen and cooled to 5° C. Then 72 g of potassium tert-butylate are added so slowly over 5 minutes that the temperature of the reaction mixture does not exceed 7° C. The mixture is then stirred for 1 h at room temperature. Then 153 g (700 mmol) of di-tert-butylcarbonate are added. The mixture is stirred for 2 h at room temperature, poured on to ice and extracted twice with ether. The organic phase is washed twice with 1N NaOH and twice with water, dried over Na$_2$SO$_4$ and concentrated by evaporation. The residue is recrystallised from hexane, giving 40 g (37%) of a crystalline substance with a melting point of 69° C.

Elemental analysis: calcd=C: 64.27, H: 7.19; found=C: 64.20, H: 7.31.
$^1$H-NMR (CDCl$_3$): $\delta$=1.55 ppm (s, 18H); $\delta$=5.29; 5.33 ppm and 5.71; 5.77 ppm (m, 2H); $\delta$=6.60-6.69 ppm (m, 1H); $\delta$=6.97-7.09 ppm (m, 3H).

II. Synthesis of the polymers

II.1. Poly[3,4-bis(2-tetrahydropyranyloxy)styrene]

To a solution of 120 g (395 mmol) of 3,4-bis(2-tetrahydropyranyloxy)styrene in 310 g of toluol is added 0.65 g of azobisisobutyronitrile. The solution is freed from oxygen by mans of a vacuum/nitrogen line. The mixture is stirred under nitrogen for 16 h at 70° C. The polymer is precipitated by pouring into n-hexane and recrystallised from THF/n-hexane. Drying under a high vacuum gives 77 g (63%) of a white powder.

Elemental analysis: calcd=C: 71.03, H: 7.95; found=C: 70.83, H: 8.06.

TGA analysis shows a weight loss of c. 56% above 220° C., indicating the thermal removal of dihydropyran.

DSC analysis shows an endothermic peak at 261° C., which is likewise attributable to the removal of dihydropyran.

A molecular weight of $M_n=20\,000$ and $M_w=61\,000$ as well as a molecular weight distribution of 3 is determined by gel permeation chromatorgraphy (GPC) in THF.

UV Absorption: a 1 μm thick film of the polymer on quartz shows an absorption of 0.12 at 250 nm. The polymer is therefore very suitable for use in DUV lithography.

II.2. Poly[3,5-bis(tetrahydropyranyloxy)styrene]

8.5 g (28 mmol) of 3,5-bis(2-tetrahydropyranyloxy)styrene are polymerised in accordance with the general procedure described in II.1.

Yield: 5 g (59%).

Elemental analysis: calcd=C: 71.03, H: 7.95; found=C: 70.89, H: 8.03.

TGA: A weight loss of c. 56% is observed in the temperature range of 190°–240° C. After the removal of dihydropyran, the polymer is stable to above 400° C.

DSC: endothermic peak at 230° C. (removal of 2 dihydropyran molecules per monomer molecule).

GPC (THF): $M_n=18\,500$; $M_w=57\,700$; molecular weight distribution: 3.1.

UV absorption: a 1 μm thick film of the polymer on quartz shows an absorption of 0.1 at 248 nm.

II.3. Poly[3,4-bis(tert-butyloxycarbonyloxy)styrene]

22 g (65 mmol) of 3,4-bis(tert-butyloxycarbonyloxy)styrene are polymerised in accordance with the general procedure described in Example II.1.

Yield: 8.5 g (40%).

Elemental analysis: calcd=C: 64.27, H: 7.19; found=C: 64.24, H: 7.21.

TGA: A weight loss of c. 60% is observed in the temperature range of 150°–180° C. (Removal of both tert-butoxycarbonyl groups).

DSC: sharp endothermic peak at 176° C.

GPC (THF): $M_n=25\,000$; $M_w=102\,000$; molecular weight distribution:4.

UV absorption: a 1 μm thick film of the polymer on quartz shows an absorption of 0.1 in the range 235–255 nm.

II.4. Poly[3,5-bis(tert-butoxycarbonyloxy)styrene]

35 g (104 mmol) of 3,5-bis(tert-butoxycarbonyloxy)styrene are polymerised in accordance with the general procedure described in Example II.1.

Yield: 15 g (43%).

Elemental analysis: calcd=C: 64.27, H: 7.19; found=C: 64.24, H: 7.23.

TGA: A sharp weight loss of c. 60% is observed from 160° C. (Removal of both tert-butoxycarbonyl groups).

DSC: sharp endothermic peak at 174° C.

GPC (THF): $M_n=20\,000$; $M_w=70\,000$; molecular weight distribution: 3.5.

UV absorption: a 1 μm thick film of the polymer on quartz shows an absorption of 0.1 in the range 235–255 nm.

III. Use Examples

III.1. 24 g of poly[3,4-bis(2-tetrahydropyranyloxy)styrene] and 1.2 g of triphenylsulfonium hexafluoroantimonate are dissolved in 170 g of cyclopentanone. This solution is filtered through a 0.5 μm filter and coated on a silicon wafer. A homogeneous film is produced on the wafer by spin coating at 2000 rpm for 20 s. The film is then dried for 1 min at 90° C. The resultant resist film has a layer thickness of 0.9 μm. The film is exposed through a chromium/quartz mask with UV radiation of 254 nm wavelength. An exposure energy of 1–3 mJ/cm² necessary. After exposure, the wafer is heated on a hot plate to a temperature of 90° C. for 10–30 s. The exposed film is then developed for 30 to 60 seconds with an aqueous-alkaline developer which is free of metal ions (Microposit MF 312), and the exposed zones are washed out. After washing with deionised water, the resist is dried for 1 minute at 100° C. Analysis of the resist structures by electron scanning microscopy shows good resolution of 0.5 μm structures.

III.2. Following the general procedure of Example III.1., a photoresist film is prepared from a solution of 2 g of poly[3,4-bis(tert-butoxycarbonyloxy)styrene] and 0.1 g of triphenylsulfonium hexafluoroarsenate in 12 g of cyclopentanone (spin-coating: 4000 rpm for 20 s, drying: 2 min/120° C., layer thickness: 0.95 μm). The resist film is exposed as in Example III.1. (254 nm, 3–4 mJ/cm², post-exposure bake for 30 s/110° C.) and developed (Selectiplast PD 2007, diluted with water to twice its volume). Structures of 0.5 μm are resolved.

III.3. Following the general procedure of Example III.1., a photoresist film is prepared from a solution of 5 g of poly[3,5-bis(tert-butoxycarbonyloxy)styrene] and 0.25 g of triphenylsulfonium hexafluoroarsenate in 25 g of cyclopentanone (spin-coating: 3500 rpm, drying: 2 min/90° C., layer thickness: 1.2 μm). The resist film is exposed as in Example III.1. (254 nm, 4–6 mJ/cm²) and developed (Microposit 312, supplied by Shipley). Structures of 0.5 μm are resolved.

III.4. Following the general procedure of Example III.1., a photoresist film is prepared from a solution of 2 g of poly[3,5-bis(tert-butoxycarbonyloxy)styrene] and 0.1 g of triphenylsulfonium triflate in 12 g of cyclopentanone (spin-coating: 3000 rpm, drying: 2 min/90° C., layer thickness: 1.05 μm). The resist film is exposed as in Example III.1. (254 nm, 10 mJ/cm², post-exposure bake for 2 min/90° C.) and developed (0.5N NaOH). Structures of 0.5 μm are resolved.

What is claimed is:

1. A polymer having a molecular weight $M_w$ of $10^3$ to $10^6$ (determined by gel permeation chromatography) and containing, based on the total amount of structural units present in the polymer, 100 to 5 mol % of a structural repeating unit of formula (VII)

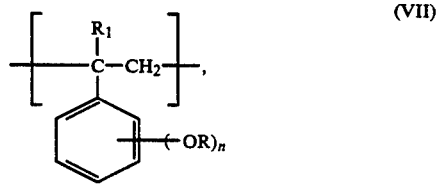

(VII)

wherein $R_1$ is hydrogen, methyl or halogen, n is 2 or 3 and R is $C_1$-$C_6$alkyl, benzyl, 2-tetrahydrofuranyl, 2-tetrahydropyranyl, $C_1$-$C_6$alkoxycarbonyl, phenoxycarbonyl or benzyloxycarbonyl, or, if two substituents OR are ortho-positioned to each other, two substituents R together form an ethylene group which may be substituted by up to four $C_1$-$C_6$alkyl groups, or form a $C_2$-$C_6$alkylidene group and 95 to 0 mol % of a structural repeating unit of formula (VIII)

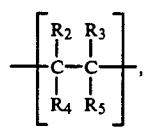
(VIII)

wherein $R_2$ and $R_3$ are each independently of the other hydrogen, $C_1$-$C_4$alkyl which is unsubstituted or substituted by halogen, cyano or nitro, or are phenyl or naphthyl which are unsubstituted or substituted by halogen, $C_1$-$C_4$alkoxy, hydroxy, cyano or nitro, and $R_4$ and $R_5$ are each independently of the other a hydrogen or halogen atom, $C_1$-$C_{12}$alkyl which is unsubstituted or substituted by halogen atoms, cyano or nitro, or are phenyl, naphthyl or benzyl which are unsubstituted or substituted by halogen, cyano or nitro, $C_1$-$C_4$alkyl or $C_1$-$C_4$alkoxy, or a radical selected from the group consisting of —$OR_6$, —$COOR_7$ and —$COR_8$ or, together with a divalent radical of formulae (IX)—(XI) are

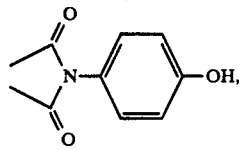
(IX)

(X)

(XI)

wherein $R_6$ and $R_7$ are each independently of the other hydrogen, $C_1$-$C_{12}$alkyl which is unsubstituted or substituted by halogen, cyano or nitro, or are phenyl or naphthyl, unsubstituted or substituted by halogen, cyano, nitro, $C_1$-$C_4$alkyl or $C_1$-$C_4$alkoxy, and $R_8$ has the same meaning as $R_6$ or is the radical

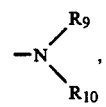

wherein $R_9$ and $R_{10}$ have each independently of the other the same meaning as $R_8$.

2. A polymer according to claim 1 containing 100 to 20 mol % of a structural repeating unit of formula (VII) and 80 to 0 mol % of a structural repeating unit of formula (VIII).

3. A polymer according to claim 1 containing a structural repeating unit of formula (VII), wherein $R_1$ is hydrogen, n is 2 and both substituents OR are in 3,4- or 3,5-position to the vinyl group.

4. A polymer according to claim 1, wherein R in formula (VII) is tert-butoxycarbonyl, 2-tetrahydrofuranyl or 2-tetrahydropyranyl.

5. A process for the preparation of a polymer according to claim 1, which comprises subjecting a compound of formula (I) according to claim 1 or a mixture of a compound of formula (I) and compounds of formula (XII)

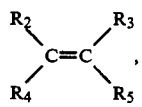
(XII)

present therein in an amount of up to 95 mol %, wherein $R_2$, $R_3$, $R_4$ and $R_5$ are as defined in claim 4, to radical polymerisation.

* * * * *